(12) United States Patent
Lindemann et al.

(10) Patent No.: US 7,875,062 B2
(45) Date of Patent: Jan. 25, 2011

(54) METHODS AND DEVICES FOR RETAINING BONE PLATE ANCHORS

(75) Inventors: Gary S. Lindemann, Collierville, TN (US); Jason Michael May, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 650 days.

(21) Appl. No.: 11/369,414

(22) Filed: Mar. 7, 2006

(65) Prior Publication Data

US 2007/0213728 A1 Sep. 13, 2007

(51) Int. Cl.
*A61B 17/80* (2006.01)
(52) U.S. Cl. .................. 606/295; 606/289; 606/280
(58) Field of Classification Search .............. 606/280, 606/289, 281, 282, 283, 285, 286, 287, 288, 606/915, 70, 71, 290–299, 284; 411/119, 411/120, 398, 374
See application file for complete search history.

(56) References Cited

U.S. PATENT DOCUMENTS

| | | | |
|---|---|---|---|
| 5,951,558 A * | 9/1999 | Fiz | 606/70 |
| 6,139,550 A * | 10/2000 | Michelson | 606/70 |
| 6,152,927 A | 11/2000 | Farris et al. | |
| 6,413,259 B1 * | 7/2002 | Lyons et al. | 606/295 |
| 6,503,250 B2 * | 1/2003 | Paul | 606/279 |
| 6,620,163 B1 * | 9/2003 | Michelson | 606/286 |
| 6,652,525 B1 | 11/2003 | Assaker et al. | |
| 6,890,335 B2 * | 5/2005 | Grabowski et al. | 606/71 |
| 6,945,973 B2 | 9/2005 | Bray | |
| 7,004,944 B2 * | 2/2006 | Gause | 606/294 |
| 7,306,605 B2 * | 12/2007 | Ross | 606/71 |
| 7,674,279 B2 * | 3/2010 | Johnson | 606/295 |
| 7,704,255 B2 * | 4/2010 | Michelson | 606/86 B |
| 2002/0022843 A1 * | 2/2002 | Michelson | 606/70 |
| 2002/0120273 A1 | 8/2002 | Needham et al. | |
| 2002/0128655 A1 * | 9/2002 | Michelson | 606/70 |
| 2002/0147450 A1 * | 10/2002 | LeHuec et al. | 606/61 |
| 2002/0183754 A1 | 12/2002 | Michelson | |
| 2002/0183755 A1 | 12/2002 | Michelson | |
| 2004/0039387 A1 * | 2/2004 | Gause et al. | 606/69 |
| 2004/0158246 A1 | 8/2004 | Assaker et al. | |
| 2004/0210217 A1 * | 10/2004 | Baynham et al. | 606/61 |
| 2004/0220571 A1 | 11/2004 | Assaker et al. | |
| 2004/0236334 A1 | 11/2004 | Michelson | |
| 2005/0059971 A1 | 3/2005 | Michelson | |
| 2005/0234455 A1 | 10/2005 | Binder et al. | |
| 2005/0283152 A1 * | 12/2005 | Lindemann et al. | 606/61 |
| 2010/0016901 A1 * | 1/2010 | Robinson | 606/289 |

* cited by examiner

*Primary Examiner*—Eduardo C Robert
*Assistant Examiner*—Jan Christopher Merene

(57) ABSTRACT

A plating system and method include a bone plate with at least a first hole therethrough between an upper surface and a lower surface of the bone plate to receive an anchor for engaging the plate to a bony segment. The system and method also include a retaining member engageable to the bone plate that includes a head with an outer perimeter having a ramped or camming portion that is positionable in contact with the anchor to prevent the anchor backing out of the first hole.

17 Claims, 6 Drawing Sheets

METHODS AND DEVICES FOR RETAINING BONE PLATE ANCHORS

BACKGROUND

Bone plates can be engaged to adjacent bony portions of a bone or of a bony segment to stabilize the bony portions. Anchors or fasteners, such as bone screws, can be used to engage bone plates to bony portions. To prevent the anchors from backing out of the plate, various retaining devices have been developed for engagement or manipulation relative to the plate adjacent to or around the bone anchors. Measures taken to retain the screws in the bone plate and keep the screws engaged in the bony portion can improve their function and avoid problems associated with bone screw backout.

There can be problems associated with prior retaining devices. For example, in prior retaining devices, the head of one or more of the anchors may interfere with positioning and alignment of the retaining device relative to the anchor. Prior retaining devices may not be employed with one or more of the anchors if the anchors move relative to the plate, or if multiple anchors associated with the retaining device are not at the same position relative to the plate. Other retaining devices include placing a retaining cover plate over the bone plate and anchors, and thus creating a higher profile bone plate that intrudes into adjacent tissue. Also, prior retaining devices can be difficult to handle, install and/or manipulate during surgery.

There remains a need for instruments and methods that can be employed for efficiently and effectively preventing backout of anchors relative to a bone plate and maintaining the engagement between the anchors and a bony segment.

SUMMARY

According to one aspect, a system involving a retaining element for a bone plate is provided. The system includes a plate with at least a first hole therethrough between an upper surface and a lower surface of the plate to receive an anchor for engaging the plate to a bony segment. The system also includes a retaining element engageable to the plate that includes a head with an outer perimeter defining an arcuate, circumferentially ramped or tapering surface that is positionable in contact with the anchor to prevent the anchor backing out of the first hole.

Another aspect involves a method for retaining at least one bone engaging anchor relative to a bone plate. The method comprises advancing the bone engaging anchor into a hole in the plate and rotating a retaining element engaged to the plate to engage an arcuate, circumferentially ramped or camming surface of the retaining element with the head of the bone engaging anchor to prevent the bone engaging anchor from backing out of the hole.

One aspect is directed to a bone plating system that includes a bone plate and at least one anchor in a hole of the bone plate. A retaining element includes a distal shank portion engaging the bone plate in a receptacle adjacent to the hole when the retaining element is rotated in a first rotational direction. The retaining element includes a proximal head portion extending about the shank portion. The head portion includes an outer perimeter extending about a rotational center of the retaining element. The outer perimeter includes at least one circular portion extending along an arc defined by a first radius extending from the rotational center and at least one camming portion forming an arcuate, circumferential surface tapering toward the rotational center.

According to another aspect, a bone plating system includes a bone plate and an anchor extending through each of at least two holes in the bone plate. A retaining element includes a distal shank portion engaging a receptacle in the plate adjacent to the plate holes by rotating the retaining element in a first rotational direction about a rotational center of the retaining element. The retaining element includes a proximal head portion extending about the shank portion. The head portion includes an outer perimeter having at least two perimeter portions extending partially about the rotational center of the retaining element along an arc defined by a radius. The outer perimeter is also interrupted by opposite first and second reliefs extending inwardly toward the rotational center. The outer perimeter also includes a first camming portion and an opposite, second camming portion that are each defined along arc that circumferentially tapers toward the rotational center. The first perimeter portion extends in the first rotational direction from the first relief to the first camming portion, and the first camming portion extends between the first perimeter portion and the second relief. The second perimeter portion extends from the second relief in the first rotational direction to the second camming portion, and the second camming portion extends between the second perimeter portion and the first relief. In use, the reliefs are positionable adjacent a respective one of the at least two holes to allow anchor insertion into the plate holes. The retaining element is rotated in the first rotational direction so that at least one of the first camming portion and the first perimeter portion contacts the anchor in one of the plate holes and at least one of the second camming portion and the second perimeter portion contacts the anchor in the other plate hole.

In yet another aspect, a method for preventing an anchor from backing out of a hole in a bone plate comprises: engaging the bone plate to a bony structure with the anchor in the hole of the bone plate; and rotating a retaining element about a rotational axis in a first direction relative to the bone plate and the anchor to position the retaining element in contact with a head of the anchor positioned in the hole of the bone plate, wherein the retaining element includes an outer perimeter having a circular portion extending partially about the rotation center and an arcuate portion that extends from the circular portion in the first direction and circumferentially tapers toward the rotational center.

These and other aspects are discussed further below.

DESCRIPTION OF THE ILLUSTRATED EMBODIMENTS

Figure 1:
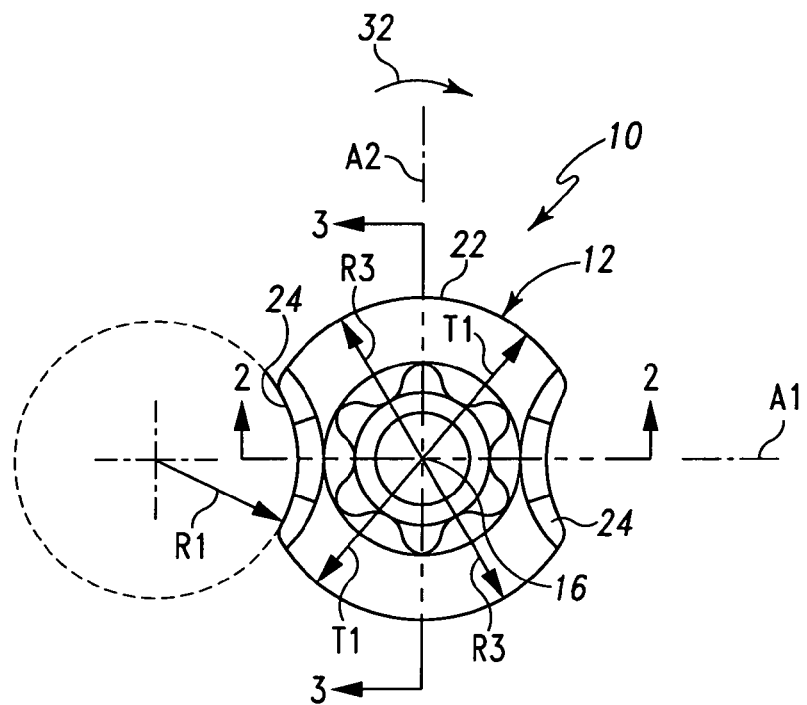
FIG. 1 is a top plan view of a retaining element.

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

Bone plates are engageable to bony segments with anchors. The bone plates are provided with one or more retaining elements configured relative to the plate holes to prevent backout of one or more anchors that engage the plate to the bony segment. The retaining elements can either contact the bone anchor, overlap the plate hole through which the anchor extends, or both. The bone plates and anchor retaining elements can be employed in the stabilization of one or more levels of the spinal column in any approach to the spinal column, including anterior, antero-lateral, lateral, posterior approaches, and in any region of the spinal column, including the cervical, thoracic, lumbar, or sacral regions. Applications in addition to or other than spinal stabilization are also contemplated.

Referring to FIGS. 1-4, retaining element 10 is shown having a proximal head portion 12 and a distal shank portion 14 extending distally from head portion 12. A central passage 16 extends through head portion 12 and shank portion 14 about a central rotational axis A3. Passage 16 opens proximally in head portion 12, and opens distally in shank portion 14. Shank portion 14 is engageable to a receptacle in a bone plate with head portion 12 extending over or adjacent to one or more holes in the plate to effectively block or prevent an anchor in the one or more plate holes from backing out or unthreading proximally relative from the plate.

Figure 2:
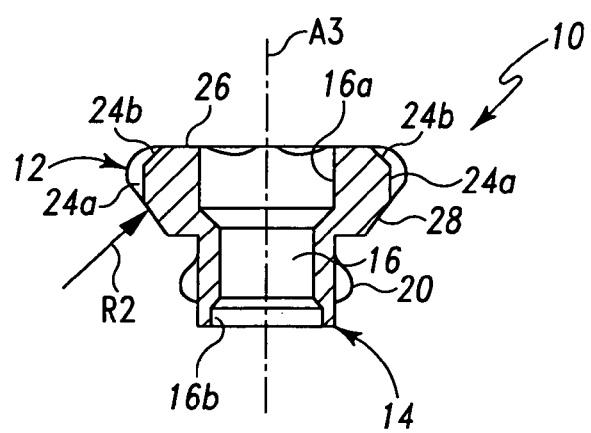
FIG. 2 is a section view through line 2-2 of FIG. 1.
Figure 3:
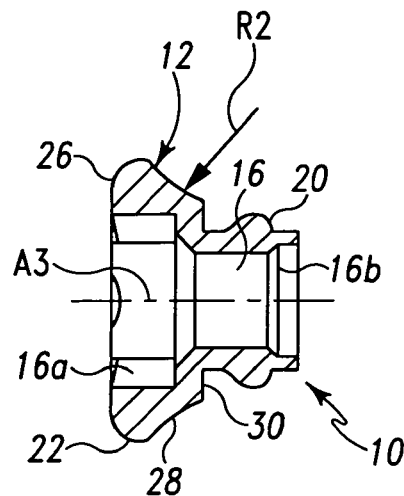
FIG. 3 is a section view through line 3-3 of FIG. 1.
Figure 4:
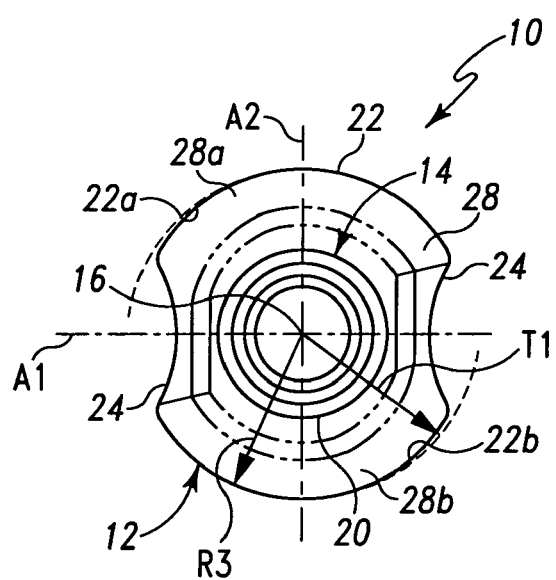
FIG. 4 is a bottom plan view of the retaining element of FIG. 1.

Retaining element 10 includes at least one external thread 20 extending about shank portion 14 for engaging a threaded receptacle in a bone plate. In addition, head portion 12 includes an outer perimeter 22 with a sidewall 28 extending thereabout. Outer perimeter 22 can also include opposite concave reliefs 24 extending into perimeter 22 toward rotational center A3. Reliefs 24 can be centered diametrically opposite one another along an axis A1 that extends through rotational center A3. Reliefs 24 can include an inwardly concave curvature or C-shape, while the portions of perimeter 22 extending between reliefs 24 can include a convexly curved shape. As shown in FIG. 2, reliefs 24 can include a vertical wall portion 24a and an upper sloped portion 24b. Sloped portion 24b extends between vertical wall portion 24a and an upper or proximal wall surface 26 of head portion 12. As shown in FIG. 1, reliefs 24 can be formed so that vertical wall portions 24a extend along an arc having a radius R1. As shown in FIGS. 2-3, sidewall 28 can be concavely curved about a radius R2 between a distal end wall surface 30 of head portion 12 and the respective adjacent vertical portions 24b, or between distal wall surface 30 and proximal wall surface 26.

Figure 5:
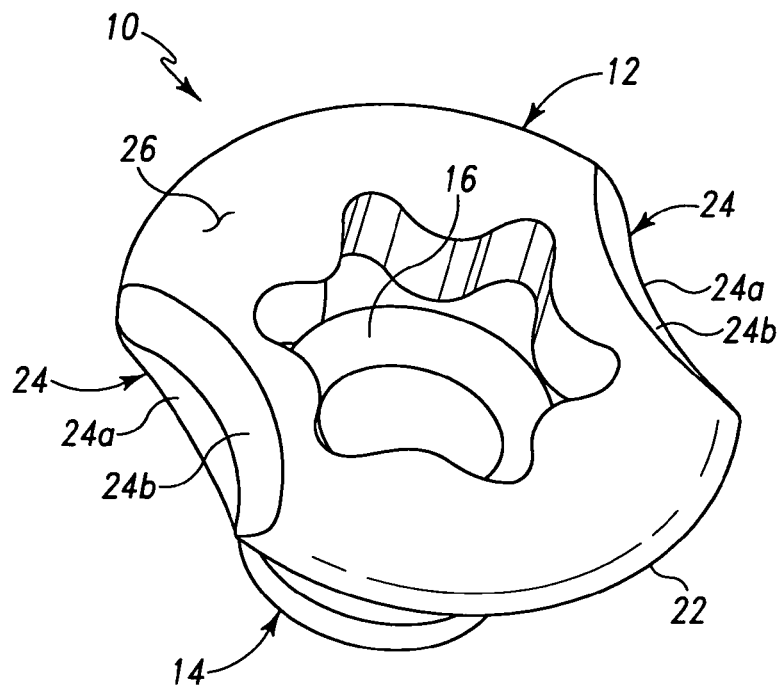
FIG. 5 is a perspective view of the retaining element of FIG. 1.
Figure 6:
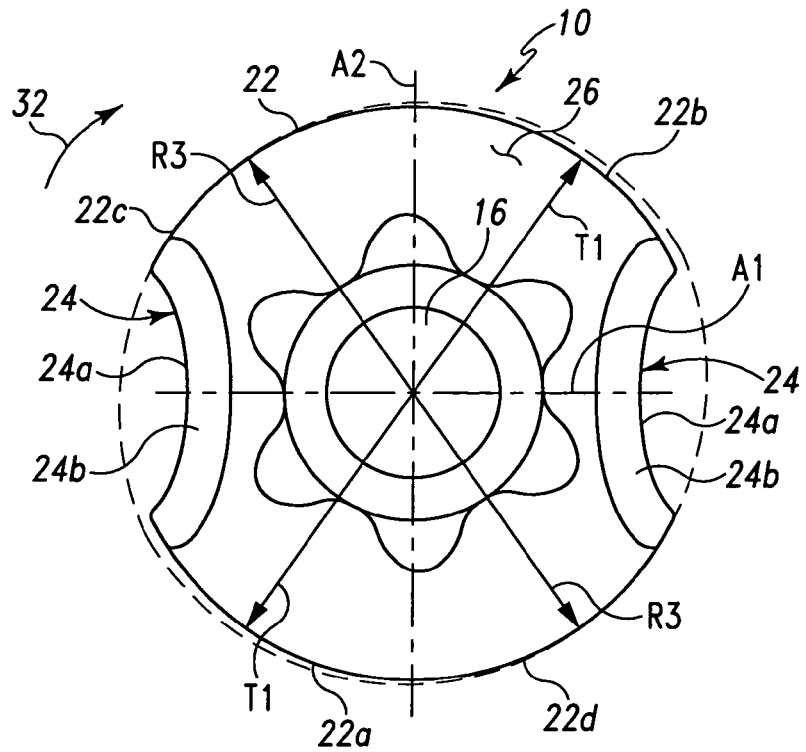
FIG. 6 is another top plan view of the retaining element of FIG. 1 showing the outer perimeter of the head portion within a circle.

As further shown in FIGS. 5-6, outer perimeter 22 includes opposite first and second perimeter portions 22c, 22d that each extend along respective ones of first and second arcs that are defined by a radius R3. The circular first and second perimeter portions 22c, 22d each extend in a first rotational direction 32 from an end of an adjacent one of the reliefs 24 to central axis A2. Central axis A2 is orthogonal to axis A1 and extends through rotational center A3. Central axis A2 is centrally located between reliefs 24 with reliefs 24 located on opposite sides of axis A2.

Outer perimeter 22 also includes first and second ramped or camming portions 22a, 22b located on opposite sides thereof. Ramped or camming portions 22a, 22b each extend along an arcuate surface that tapers circumferentially inwardly toward rotational center A3. Accordingly, ramped or camming portions 22a, 22b do not extend along an arc defined by a constant radius, but rather are defined by a "radius" that is a taper T1 progressively and constantly decreasing along camming portions 22a, 22b in first direction 32. Accordingly, the taper T1 is equal to radius R3 at central axis A2, and tapers to a minimum dimension along axis A1. The arcuate surfaces defined along the respective camming portions 22a, 22b can extend from an end of the adjacent outer perimeter portion 22c, 22d on central axis A2 in first direction 32 to an end of the adjacent relief 24. Sidewall 28 can also include sidewall portions 28a, 28b (FIG. 4) that extend along and follow the respective adjacent camming portion 22a, 22b.

Passage 16 includes a proximal tool engaging portion 16a and a distal flared portion 16b. Tool engaging portion 16a can open through proximal wall surface 26 of head portion 12. In the illustrated embodiment, tool engaging portion 16a forms an internal recess that includes a shape configured to engage a driving tool that supplies the necessary force to rotate retaining element 10 relative to the bone plate from an open position where reliefs 24 are adjacent the plate holes to permit anchor insertion to the closed position to a closed position where perimeter 22 contacts the anchors in the plate holes. Tool engaging portion 16a can include a star shape, hexagonal shape, cross-shape, slotted shape, or any other suitable shape to engage a driving tool. Other embodiments contemplate that the tool engaging portion 16a forms an external shape to receive a driving tool.

Distal flared portion 16b can be deformed outwardly to stake or secure retaining element 10 in a desired position relative to the plate. In particular, retaining element 10 can be staked to the plate in the open position so that it frictionally engages the plate and is maintained in the open position until sufficient force is applied to overcome the frictional engagement and rotate retaining element 10 to the closed position.

Figure 7:
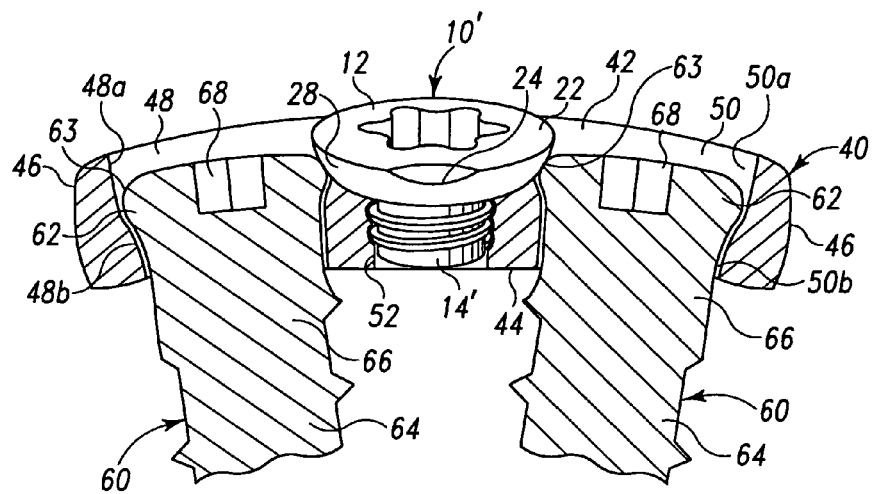
FIG. 7 is a section view of a bone plate and bone anchors extending through the bone plate engaged by a retaining element in a closed position.
Figure 8:
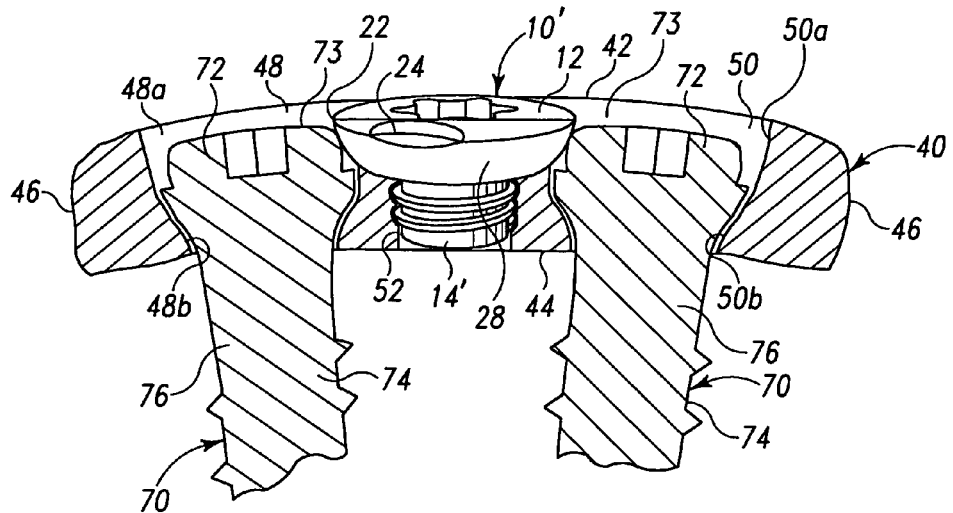
FIG. 8 is a section view of the bone plate and another embodiment bone anchors extending through the plate engaged by the retaining element of FIG. 7 in a closed position.

In FIGS. 7 and 8, there is shown another embodiment retaining element 10' engaged to a plate 40. Retaining element 10' is similar to retaining element 10, but includes a shaft portion 14' having multiple thread turns thereabout. Head portion 12 can be identical to head portion 12 of retaining element 10 discussed above. Bone plate 40 includes an upper or proximal surface 42, a lower or distal bone contacting surface 44, and opposite sidewalls 46 extending between upper and lower surfaces 42, 44. Plate 40 also includes a first hole 48 and a second hole 50 for receiving bone anchors. A receptacle 52 is located between holes 48 and 50 for receiving retaining element 10, 10' therein. Receptacle 52 can include threads or other suitable configuration for engagement of shaft portion 14, 14'.

Retaining element 10, 10' can be engaged to plate 40 with reliefs 24 positioned adjacent to respective ones of the holes 48, 50 so that the relief extends about a portion of the perimeter of the respective adjacent hole. In this open position, holes 48, 50 are not blocked or obstructed by retaining element 10, 10', and anchors 60 can be inserted through respective ones of the holes 48, 50.

Anchors 60 each include a proximal head 62 and a distal shaft 64. Shaft 64 can include a thread profile to threadingly engage a bony structure, such as a vertebra, underlying plate 40. An intermediate neck 66 extends between head 62 and shaft 64. Head 62 includes a tool engaging recess 68 extending therein and opening proximally to receive a driving tool. Anchors 60 can be inserted through respective ones of the holes 48, 50 so that head 62 is received in a proximal, recessed portion 48a, 50a of the respective hole 48, 50 and neck 66 contacts a distal cylindrical portion 48b, 50b of the respective hole 48, 50. Contact between neck 66 and the adjacent cylindrical portion 48b, 50b fixes the angular orientation of shaft 64 relative to plate 40 and its bottom surface 44. The distally oriented surface of head 62 can be convexly curved to seat within a concavely curved, spherically shaped proximal portion 48a, 50a.

In FIG. 7 retaining element 10' has been rotated on plate 40 so that sidewall 28 along the outer perimeter of head portion 12 contacts an edge 63 extending about head 62 of anchor 60. Relief 24 is located between holes 48, 50 since retaining element 10' has been rotated about its central axis A3 in the first rotational direction to advance retaining element 10' into receptacle 52. Since the radial dimension of the camming portions of the retaining element 10, 10' gradually increases about outer perimeter 22 in the direction opposite the first rotational direction, retaining element 10, 10' can be rotated in the first rotational direction until firm engagement between head portion 12 of retaining element 10, 10' and heads 62 of anchors 60 is achieved.

Referring now to FIG. 8, there is shown another embodiment anchor engaged to plate 40 to secure it to a bony segment such as the spinal column. Anchors 70 each include a proximal head 72, a distal shaft 74 for threadingly engaging bony structure, and an intermediate neck 76 between head 72 and shaft 74. The diameter of the neck 76 can be substantially smaller than the size of distal cylindrical portion 48b, 50b of holes 48, 50 so that anchor 70 can pivot in the respective hole 48, 50 when seated therein and shaft 74 can assume any one of a number of angular orientations relative to bottom surface 44 of plate 40. After insertion of anchors 70 into respective ones of the plate holes 48, 50, retaining element 10, 10' can be rotated so that head portion 12 contacts a proximally facing, spherically shaped or curved surface of head 72 of each of the anchors 70. Since retaining element 10, 10' is seated on the proximally oriented surfaces of heads 72, the angular orientation of anchors 70 in holes 48, 50 does not effect the locking ability of retaining element 10, 10'. Retaining element 10, 10' can be rotated until outer perimeter 22 firmly engages and contact anchors 70 in holes 48, 50 to lock the anchors 70 in position relative to plate 40. In another embodiment, one of the holes 48, 50 includes an anchor 60 and the other includes an anchor 70.

The cammed or ramped portions 22a, 22b of outer perimeter 22 provide a variable surface profile about head portion 12 that can contact anchors 60, 70 even if the tolerances between the plate, anchor and retaining element provide less than optimal placement of the components relative to one another. For example, the circular outer perimeter portions 22c, 22d can be sized to contact the anchors at the outer limits of the tolerances so that contact with retaining element 10, 10' and anchors 60, 70 can be achieved. If the tolerances fall within the outer limits, the variable camming or ramped portions 22a, 22b can contact the anchors 60. 70.

Figure 9:
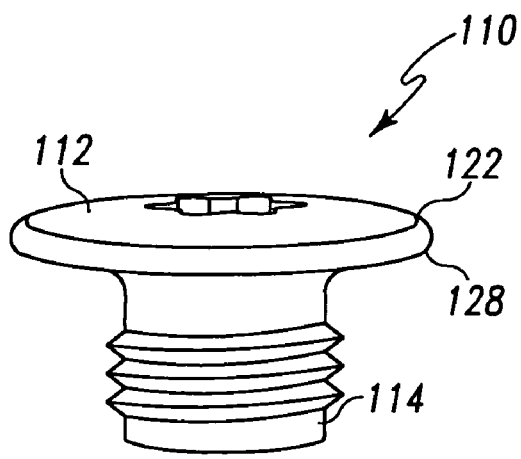
FIG. 9 is an elevation view of another embodiment retaining element.
Figure 10:
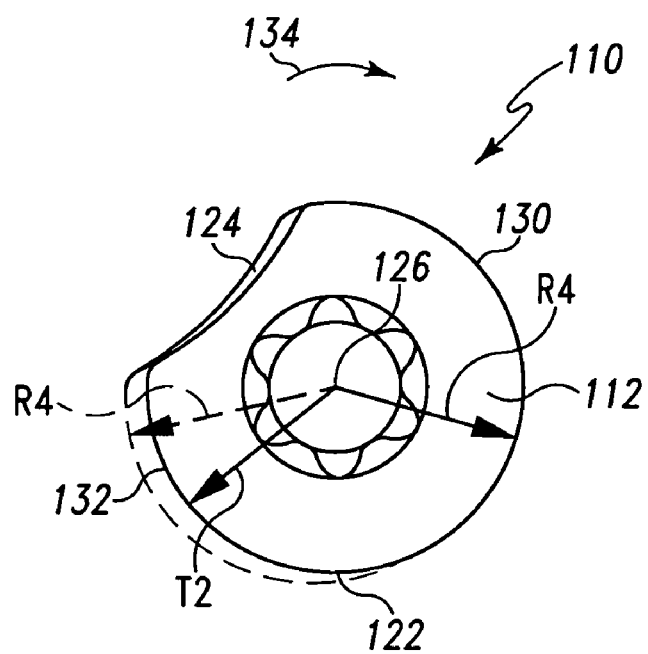
FIG. 10 is a top plan view of the retaining element of FIG. 9.

Referring now to FIGS. 9-10, another embodiment retaining element 110 is shown. Retaining element 110 includes a proximal head portion 112 and a distal shaft portion 114 having an external thread profile to engage a receptacle in a bone plate when rotated in a first direction 134 about its rotational center 126. Head portion 112 can be similar to head portion 12 discussed above, but includes a single relief 124 in its outer perimeter 122. Outer perimeter 122 includes a sidewall 128 extending between proximally and distally oriented wall surfaces of head portion 112.

Sidewall 128 extends along a first perimeter portion 130 that is defined by an arc having a radius R4 extending through rotational center 126 of retaining element 110. Outer perimeter 122 also includes an arcuate ramped or camming portion 132 that extends from first perimeter portion 130 in the rotational direction 134 to relief 124. Camming portion 132 defines an arcuate surface that circumferentially tapers in rotational direction 134 such that radius T2 is variable and radially decreases in first direction 134. Sidewall 128 extends along and follows first perimeter portion 130 and camming portion 132.

Figure 11:
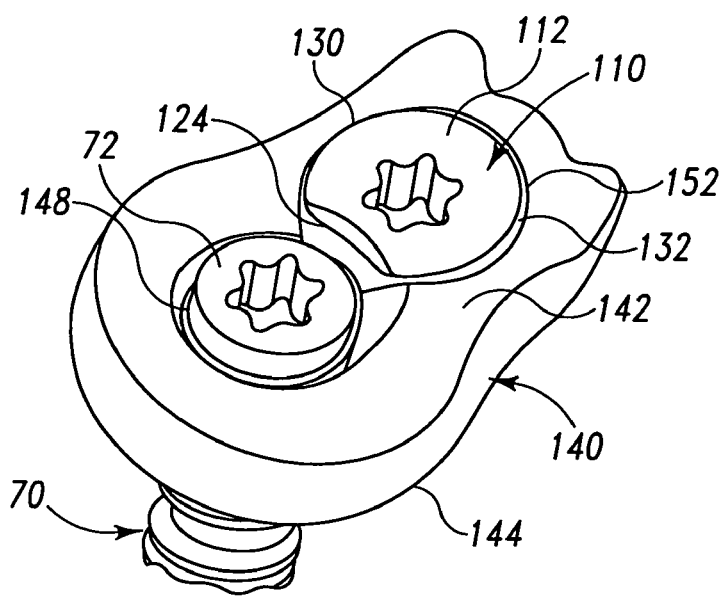
FIG. 11 is a perspective view of a portion of another embodiment plate and anchor with the retaining element of FIG. 9 engaged to the plate in an open position.
Figure 12:
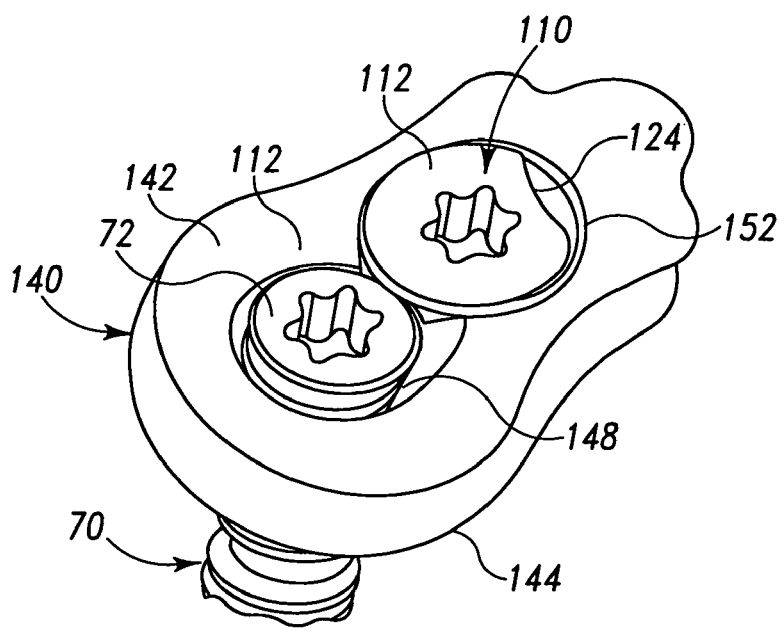
FIG. 12 is the plate and anchor portion of FIG. 11 with the retaining element of FIG. 9 engaged to the plate in a closed position.

In FIGS. 11-12, retaining element 110 is shown engaged to a receptacle 152 of a bone plate 140. Plate 140 includes an upper or proximal surface 142 and a lower or distal surface 144. A hole 148 extends between upper and lower surfaces 142, 144 and can receive a bone anchor such as bone anchor 70. Retaining element 110 can be engaged to receptacle 152 of plate 140 in a first or open position, as shown in FIG. 11, where hole 148 is not obstructed or blocked by retaining element 110 to permit passage of anchor 70 into hole 148. When the head of anchor 70 is seated in hole 148, retaining element 110 can be rotated in the first rotational direction 134 (clockwise in the illustrated embodiment) to a closed position as shown in FIG. 12. In the closed position, retaining element 110 can extend into or overlap hole 148 and contact bone engaging anchor 70 to prevent anchor 70 from backing out of the plate hole. Retaining element 110 can be rotated until one of the camming portion 132 and outer perimeter portion 130 contacts head 72.

The bone plates herein are shown in partial views, but may include any suitable overall shape and form for plates for spinal stabilization, including plates employed for anterior, antero-lateral, lateral, and posterior stabilization procedures. The plate holes for receiving the anchors can be generally circular; however, it should be appreciated that the holes can be configured or shaped differently in any manner suitable for receipt of an anchor. For example, the holes can be cylindrical, partially spherical, frusto-conical, elongated, oval, slotted, and combinations thereof. Further, it should be appreciated that additional holes can be provided through the bone plates, either in isolation, in adjacent hole pairs, or three or more adjacent holes. The plates discussed herein can be made from any one or a combination of suitable material or materials, including metals and metal alloys, polymers, biological materials, synthetic materials, and resorbable materials, for example.

The anchors can include a proximal head and a distal bone engaging portion. The bone engaging portion can include a thread pattern therealong to engage bony structure. In the illustrated embodiments, the bone engaging portion of the anchors includes an elongated shaft structure with a generally cylindrical shape, although other shapes are also contemplated, including circular, square, rectangular, polygonal shape, and any other suitable shape for passage through a plate hole and engagement with bony structure. When positioned in the plate hole, the head of the anchor can be fixed, pivotal, translatable or otherwise movable in the hole. It is contemplated that the head can extend at or at least slightly above the upper proximal surface of the plate, or could be recessed distally below the upper surface.

The use of a plating system by a surgeon may involve inserting retaining member 10, 10', 110 in a receptacle in the plate after placement of one or more anchors in the holes of the plate. However, the reliefs about the perimeter of retaining members 10, 10', 110 allow the retaining member to be pre-assembled or attached to a receptacle in the plate before placing the plate in the patient along the bone segment to be stabilized. This minimizes the fiddle factor to the surgeon during the procedure. Handling of plating system is further facilitated since the retaining member need only be moved less than one complete turn from the open position to the closed position to engage the anchor or anchors.

After implantation and securement of the bone plate to the bony structure, the retaining element prevents and/or limits the backout of one or more anchors relative to the plate. Specifically, the interference between the retaining element and the head of the anchor blocks the anchor from backing out of the plate hole and out of engagement with bony structure underlying the plate and into tissue surrounding the plate. Contact between the anchor or anchors and the retaining element can maintain the retaining element in position after it has been moved to the closed position. Alternatively or additionally, the retaining element can include a locking thread pattern, a crimp, a wedge, a stake or other structure to engage the bone plate that resists reverse rotation of the retaining element relative to the bone plate from the closed position.

While the invention has been illustrated and described in detail in the drawings and foregoing description, the same is to be considered as illustrative and not restrictive in character. For example, the retaining elements can include three or more reliefs about the perimeter of the head portion. Also, the retaining elements could be configured to be rotated in the counterclockwise direction on the plate to secure the retaining element to the one or more bone anchors. All changes and modifications that come within the spirit of the invention are desired to be protected.

What is claimed is:

1. A bone plating system, comprising:
   a bone plate including at least one hole therethrough between an upper surface and a lower surface of said bone plate to receive an anchor for engaging said bone plate to a bony segment, said bone plate including at least one receptacle adjacent to said first hole; and
   a retaining element including a distal shank portion engaging said bone plate in said receptacle when rotated in a first rotational direction about a rotational center of said retaining element, said retaining element including a proximal head portion extending about said shank portion, said head portion including a top surface opposite said distal shank portion positioned adjacent said upper surface of said bone plate, wherein when viewed in a direction looking along said rotational center toward said top surface said head portion includes:
      an outer perimeter extending about said rotational center of said retaining element, said outer perimeter including a first perimeter portion visible from said direction that extends along an arc defined by a first radius extending through said rotational center, said outer perimeter further including a camming portion extending from said first perimeter portion that is formed by an arcuate surface that includes a circumferential taper visible from said direction that tapers toward the rotational center in the first rotational direction,
      at least one of said camming portion and said first perimeter portion is positionable relative to said plate when said retaining element is rotated in the first rotational direction to contact said anchor in said at least one hole of said bone plate, and
      a relief along said outer perimeter that extends from said camming portion inwardly toward said rotational center, said retaining element being positionable relative to said bone plate in an open position wherein said relief is configured to permit the anchor to be positioned into said at least one hole from said upper surface of said bone plate, said retaining element being rotatable relative to said bone plate in said first rotational direction from said open position to contact at least one of said camming portion and said first perimeter portion with a head of said anchor in said hole of said bone plate;
   wherein said retaining element includes a first axis extending through said rotational center and bisecting said relief and a second axis orthogonal to said first axis and orthogonal to said rotational center, wherein said arcuate surface of said camming portion circumferentially tapers on said outer perimeter at least from said second axis to said relief in said first rotational direction so that a radius of said outer perimeter where said camming portion joins said relief is less than said first radius of said first perimeter portion extending from said camming portion.

2. The system of claim 1, wherein said arcuate surface extends in said first rotational direction from an end of said first perimeter portion.

3. The system of claim 2, wherein said relief includes a concavely curved shape.

4. The system of claim 2, wherein said relief includes a concavely curved, vertically extending wall portion and a sloped wall portion, said vertically extending wall portion extending proximally from a distally oriented wall surface of said head portion and said sloped wall portion extending between said vertically extending wall portion and a proximally oriented wall surface of said head portion.

5. The system of claim 2, wherein said head portion includes a second inwardly extending relief along said outer perimeter opposite the other relief and said bone plate includes a second hole between said upper and lower surfaces of said plate for receiving a second anchor, said reliefs being positionable adjacent respective ones of said first and second holes when said retaining element is in said open position to permit placement of anchors into each of the holes from said upper surface of said bone plate.

6. The system of claim 5, wherein said outer perimeter includes:
   a second perimeter portion opposite said first perimeter portion, said first perimeter portion extending from said first relief in said first rotational direction and said second perimeter portion extending from said second relief in said first rotational direction; and
   a second camming portion about said outer perimeter opposite said camming portion, said second camming portion extending between said second perimeter portion and said first relief and said camming portion extending between said first perimeter portion and said second relief.

7. The system of claim 1, wherein said shank portion includes an outer thread profile that threadingly engages said bone plate in said receptacle.

8. The system of claim 1, wherein said retaining element includes a central passage extending therethrough along said rotational axis.

9. The system of claim 8, wherein said head portion includes a distal wall surface extending about said shank portion and said top surface is an opposite, proximally oriented wall surface, said head portion further including a sidewall extending between said distal and proximal wall surfaces having a concavely curved profile between said distal and proximal wall surfaces.

10. The system of claim 9, wherein said sidewall extends along said first perimeter portion and said camming portion.

11. A bone plating system, comprising:
a bone plate including at least two holes therethrough between an upper surface and a lower surface of said bone plate, each of said holes to receive an anchor for engaging said bone plate to a bony segment, said bone plate including at least one receptacle between said pair of holes;
a retaining element including a distal shank portion engaging said plate in said receptacle when rotated in a first direction about a rotational center of said retaining element and a proximal head portion extending about said shank portion, said proximal head portion including a top surface opposite said distal shank portion, said top surface positioned adjacent said upper surface of said bone plate, wherein when viewed in a direction looking along said rotational center toward said top surface said head portion includes an outer perimeter that is visible from said direction, said outer perimeter extending about said rotational center of said retaining element, said outer perimeter being interrupted by a first relief extending inwardly toward said rotational center and a second relief opposite said first relief extending inwardly toward said rotational center, said outer perimeter further including:
a first perimeter portion visible from said direction that extends partially about said rotational center along a first arc defined by a first radius extending from said rotational center, said first perimeter portion extending from said first relief in said first direction;
a second perimeter portion visible from said direction that extends partially about said rotational center along a second arc defined by said first radius, said second perimeter portion extending from said second relief in said first direction;
a first camming portion that is visible from said direction that extends along a first arcuate surface between said first perimeter portion and said second relief, said first arcuate surface including a circumferential taper that is visible from said direction that tapers toward said rotational center in said first direction; and
a second camming portion visible from said direction that extends along a second arcuate surface between said second perimeter portion and said first relief, said second arcuate surface including a circumferential taper that is visible from said direction that tapers toward said rotational center in said first direction, wherein at least one of said first perimeter portion and said first camming portion is positionable in contact with the anchor in one of said at least two holes while at least one of said second perimeter portion and said second camming portion is positionable in contact with the anchor in the other of said at least two holes;
wherein said retaining element includes a first axis extending through said rotational center and bisecting first and second reliefs and a second axis orthogonal to said first axis and orthogonal to said rotational center, wherein said first arcuate surface of said first camming portion circumferentially tapers on said outer perimeter at least from said second axis to said second relief in said first direction and said second arcuate surface of said second camming portion circumferentially tapers at least from said first axis to said first relief in said first direction so that a radius of said outer perimeter where said first and second camming portions join respective ones of said second and first reliefs is less than said first radius of said outer perimeter where said first and second perimeter portions join respective ones of said first and second reliefs.

12. The system of claim 11, wherein said first and second reliefs are each generally C-shaped.

13. The system of claim 11, wherein said shank portion of said retaining element includes an outer thread profile and threadingly engages said plate in said receptacle.

14. The system of claim 11, wherein said head portion of said retaining element includes a distally oriented wall surface extending about said shank and said top surface includes an opposite proximally oriented wall surface, said head portion further including a sidewall extending between said distal and proximal wall surfaces, at least a portion of said sidewall including a concavely curved profile that extends between said distal and proximal wall surfaces.

15. The system of claim 14, wherein said sidewall extends along said first and second perimeter portions and said first and second camming portions.

16. The system of claim 15, wherein said sidewall tapers toward said rotational center from said proximal wall surface toward said distal wall surface.

17. The system of claim 11, wherein at least one of said first and second reliefs includes a concavely curved, vertically extending wall portion and a sloped wall portion, said vertically extending wall portion extending proximally from a distally oriented wall surface of said head portion and said sloped wall portion extending between said vertically extending wall portion and a proximally oriented wall surface of said head portion.

* * * * *

UNITED STATES PATENT AND TRADEMARK OFFICE
CERTIFICATE OF CORRECTION

| | | |
|---|---|---|
| PATENT NO. | : 7,875,062 B2 | Page 1 of 1 |
| APPLICATION NO. | : 11/369414 | |
| DATED | : January 25, 2011 | |
| INVENTOR(S) | : Lindemann et al. | |

It is certified that error appears in the above-identified patent and that said Letters Patent is hereby corrected as shown below:

In Column 9, Line 48, in Claim 11, delete "said first" and insert -- a second --, therefor.

In Column 9, Line 50, in Claim 11, delete "direction;" and
insert -- direction, wherein said second radius is equal to said first radius; --, therefor.

Signed and Sealed this
Twelfth Day of July, 2011

David J. Kappos
*Director of the United States Patent and Trademark Office*